United States Patent [19]

West

[11] Patent Number: 5,352,116
[45] Date of Patent: Oct. 4, 1994

[54] ADJUSTABLE BITE CORRECTOR

[76] Inventor: Richard P. West, 3115 Montecito Meadow Dr., Santa Rosa, Calif. 95404

[21] Appl. No.: 163,368

[22] Filed: Dec. 6, 1993

[51] Int. Cl.$^5$ .............................................. A61C 3/00
[52] U.S. Cl. .................................................... 433/19
[58] Field of Search ............................. 433/18, 19, 21

[56] References Cited

U.S. PATENT DOCUMENTS

| | | |
|---|---|---|
| 3,618,214 | 11/1971 | Armstrong . |
| 3,798,773 | 3/1974 | Northcutt .............................. 433/19 |
| 4,708,646 | 11/1987 | Jasper .................................... 433/19 |

Primary Examiner—Cary E. O'Connor
Attorney, Agent, or Firm—Larry D. Johnson

[57] ABSTRACT

An orthodontic appliance to aid in the correction of certain types of malocclusions applies a force within a patient's mouth that urges one jaw of a patient having an overbite or underbit condition relative to the other jaw generally along his or her normal growth axis. The appliance is constructed so that it is stretchable and has a degree of flexibility, and includes end attachment means which enables it to turn or swivel adjacent its anchor points on the upper and lower jaws of the patient. Thus, a patient can wear a pair of appliances with a minimum of discomfort while retaining the ability to talk, chew food and perform normal oral hygiene procedures such as tooth brushing when necessary.

3 Claims, 4 Drawing Sheets

ADJUSTABLE BITE CORRECTOR

BACKGROUND OF THE INVENTION

1. Field of the Invention

This invention relates generally to orthodontic appliances, and more specifically to an improved overbite and underbite corrective device.

2. Description of the Prior Art

Numerous orthodontic appliances have been developed to treat malocclusions of the upper and lower jaw. For example, Armstrong U.S. Pat. No. 3,618,214 discloses a coiled wire appliance utilizing small springs inside plastic tubes to pull the jaws together. More recently, Jasper U.S. Pat. No. 4,708,646 teaches the use of one or more flexible members which are attached at opposite ends to the upper and lower jaws of a patient. The end attachments allow the members to swivel freely and the members to bend when the patient is chewing, talking, or cleaning his or her teeth, but when the patient is relaxed, the members tend to straighten and apply a small but continuous force generally along the normal growth direction for a human jaw to overcome the abnormality being treated. However, these flexible members are specifically non-stretching, which limits their use in certain corrective applications. In addition, the Jasper appliance is not adjustable in length, necessitating a variety of sizes to fit different users. Furthermore, the Jasper device is often difficult to install in a patient's mouth, and is prone to breakage.

SUMMARY OF THE INVENTION

The adjustable bite corrector of this invention provides an orthodontic appliance to aid in the correction of certain types of malocclusions formerly treated with a headgear type appliance and requiring patient cooperation. The inventive device functions to apply a force within a patient's mouth that urges one jaw of a patient having an overbite or underbite condition relative to the other jaw generally along his or her normal growth axis. The appliance is constructed so that it is stretchable and has a degree of flexibility, and includes end attachment means which enables it to turn or swivel adjacent its anchor points on the upper and lower jaws of the patient. Thus, a patient can wear a pair of appliances with a minimum of discomfort while retaining the ability to talk, chew food and perform normal oral hygiene procedures such as tooth brushing when necessary.

Each appliance, according to the invention, comprises an elongated, generally cylindrical stretchable and somewhat flexible device, having fixed end caps, at least one of which is adjustable in length, each with an attachment flange that extends at an angle to the axial centerline of the elongated device. An opening is provided in each attachment flange. For example, in an installation in a patient to treat an overbite condition, one attachment flange is connected to a rearward or distal anchor located distally on the upper jaw near the patient's upper molars. The other attachment flange of the device is retained by a forward or mesial anchor located on the patient's lower jaw near the lower bicuspid teeth. The mesial anchor may be a structural member such as a small metal jig fixed to a suitable wire such as an arch wire or an extension thereon attached to normal braces on the patient's teeth. The distal anchor may be a small ball fixed to an adjustable rear jig or wire that is retained within the molar tube attached to the patient's upper jaw teeth. The length of the rear wire and thus the position of the distal anchor can be adjusted so that each appliance is essentially straight and exerts a small axial force against the patient's lower jaw to hold the jaw in the normal bite position. Since this corrective force is exerted along the normal growth line of the jaw during a high percentage of the time that it is worn, and a pair of appliances can normally be worn constantly without discomfort, they are highly effective in correcting the overbite condition within a relatively short period as opposed to prior techniques. Variations in anchoring means can be provided within the scope of the invention to accommodate patients with or without braces and in either case, the appliances can be installed quickly and easily adjusted by a skilled orthodontist.

The inventive device differs from prior art devices in the following areas:

I. Stretchable

The open coil design of the highly resilient wire used allows the device to stretch 25% to 50% over its initial length and return to that same prestretched length or configuration without distortion. This feature allows its use with less pull or dislodging at the upper point of attachment which has been a problem with prior art devices. This feature will prevent loss of function, injury to the patient and loss of control between adjustment or observation appointments.

The stretchability can also be utilized when placing the device for those users who prefer to use a pull force between the dental arches versus those who prefer a push force between arches. The difference here is in the points of attachment; a pull force to correct the overbite would require attachment from the lower posterior molar band to the upper anterior point of attachment of the wire jig described later.

II. Adjustable

The threaded end cap element attached at one end of the push coil arrangement allows the device to be placed at a given functioning length and later have that length increased by a calibrated measured amount to increase the force by increasing the overall length. A raised notch on the threaded end and on the end caps permits fine calibration when increasing or decreasing the length and forces.

Alternatively, the device can be placed in the extended length configuration by opening the threaded end several millimeters at initial placement, and later closing the threaded end to be able to reduce the forces during a period of adjustment to the correction achieved. In other words, the device can be shortened after it has accomplished the amount of correction desired by turning the threaded attachment counter-clockwise and using it to "hold" the jaw and tooth position. These same principles of use can be applied to the device when used as a pull force between the dental arches, once again depending upon the points of attachment and the desired treatment effect.

III. Less Breakable

Due to the stretchable open coil spring design using highly resilient wires for fabrication, the inventive device is not easily broken when the patient opens his or her mouth beyond what the fixed length of the prior art devices can tolerate without permanently deforming or pulling apart at the point where the rubber joins the end cap attachments. The spring will elongate with excess opening and return to its original length when the patient relaxes or closes his or her mouth. The coil spring design allows the device to be rigidly fixed at either end either intentionally or unintentionally and continue to operate as a swivel due to the flexible nature of the spring design.

The design of the stainless steel wire jigs fabricated of wire of sufficient diameter to prevent breakage also reduces failure of the device. Their use allows the patient greater range of motion when opening by permitting the device to slide along the length of the jig without binding and breaking.

IV. Universal Right and Left

Any single device can be used on either side of the mouth without causing the device to flex or bow in toward the patient's biting surfaces thus reducing error in placement, selection and reduced inventory requirements. If placed incorrectly by the user or assistant, the device will adjust and rotate to the desired configuration. Thus, there is no right or left nor an up or down end to the device.

V. Easily Placed and Removed

The use of the wire jigs allow the device to be attached in various arrangements external to the existing braces, thus eliminating the need to remove the arch wire or any of the fixed braces. The jig can be fabricated to attach to the hook on the lower molar band found on most molar braces. The jig can also be attached by a steel tie wire from the "eyelet" portion to the molar band hook. The jig can be fabricated to attach without the use of the molar band hook by using alternate designs. Different jig designs can be used to create a more horizontal or more vertical force if so desired.

DETAILED DESCRIPTION OF A PREFERRED EMBODIMENT

Figure 1:
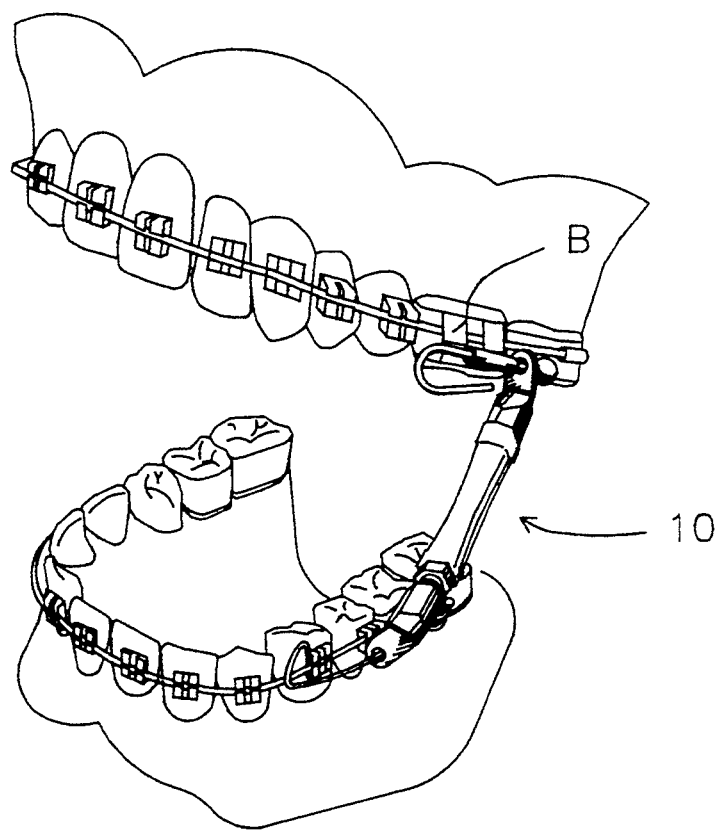
FIG. 1 is a perspective view of an adjustable bite corrector of this invention as installed on the braces in a patient's open mouth, illustrating the device in its unflexed configuration.
Figure 2:
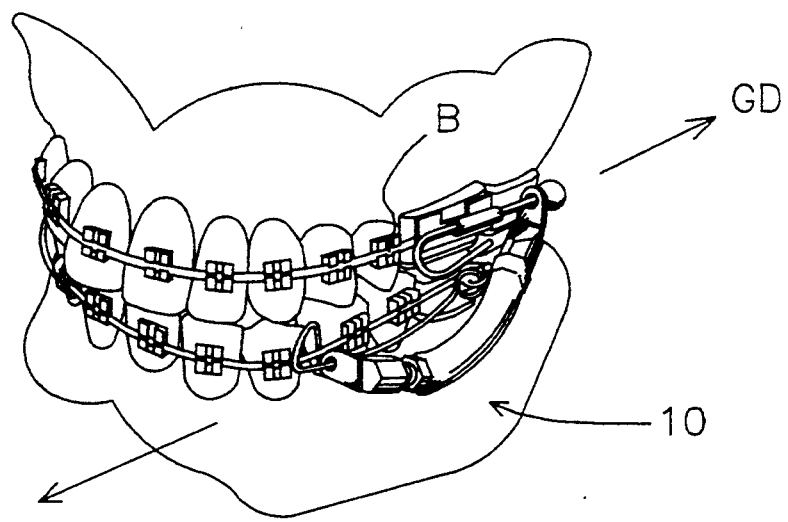
FIG. 2 is a perspective view of the adjustable bite corrector of this invention as installed on the braces of a patient's closed mouth, illustrating the device in its flexed configuration and exerting a small but continuous force generally along the normal growth direction for a human jaw.

FIG. 1 is a perspective view of the adjustable bite corrector 10 of this invention as installed to the braces B in a patient's open mouth, illustrating the device in its unflexed configuration, while FIG. 2 illustrates the device 10 in its flexed configuration (mouth closed) and exerting a small but continuous force generally along the normal growth direction GD for a human jaw.

Figure 3:
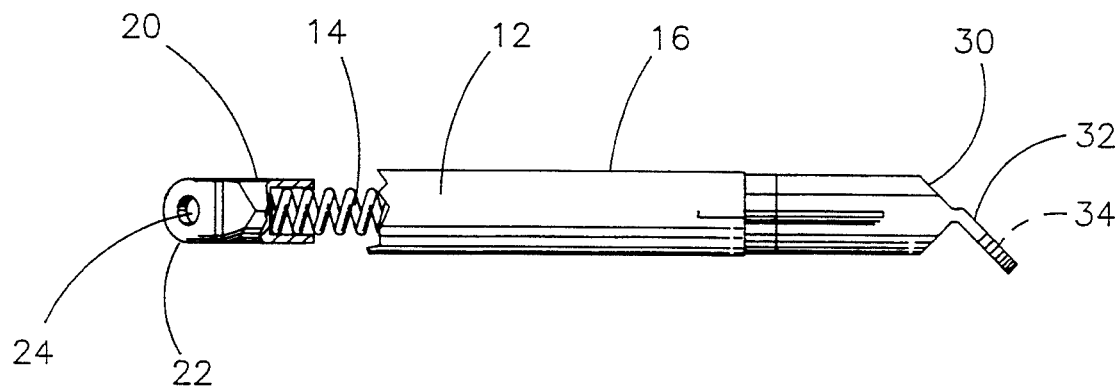
FIG. 3 is a partially cutaway side elevation view of the adjustable bite corrector of this invention in its minimum length adjustment.

FIG. 3 is a partially cutaway side elevation view of the adjustable bite corrector 10 of this invention in its minimum length adjustment. The device includes a flexible, stretchable body portion 12 comprising a coil spring 14 covered by a plastic sleeve 16. End caps 20, 30 are mounted to the ends of the body, and each present an angled flange 22, 32 bearing an eyelet 24, 34 that can be attached to a user's braces, as described supra.

Figure 4:
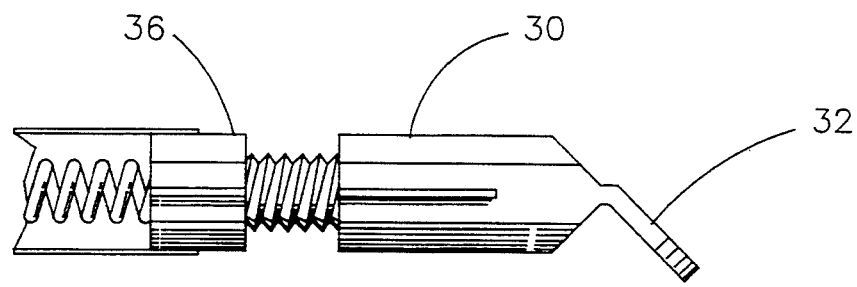
FIG. 4 is a partially cutaway side elevation view of an adjustable end cap of this adjustable bite corrector of this invention, illustrating the length adjustment feature determined by the threaded connection of the end cap to the cap base.

FIG. 4 is a partially cutaway side elevation view of an adjustable end cap 30 of this adjustable bite corrector of this invention, illustrating the length adjustment feature determined by the threaded connection of the end cap 30 to the cap base 36. This threaded adjustment may enable plus or minus three millimeters of length.

Figure 5:
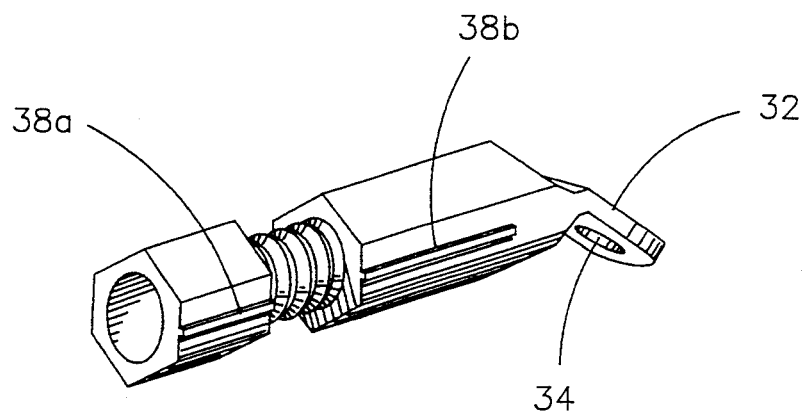
FIG. 5 is a perspective view of an adjustable end cap of the adjustable bite corrector of this invention illustrating the raised notches used to permit calibration of the length adjustment.

FIG. 5 is a perspective view of an adjustable end cap 30 of the adjustable bite corrector of this invention illustrating the raised notches 38 a, b used to permit calibration of the length adjustment.

Figure 6:
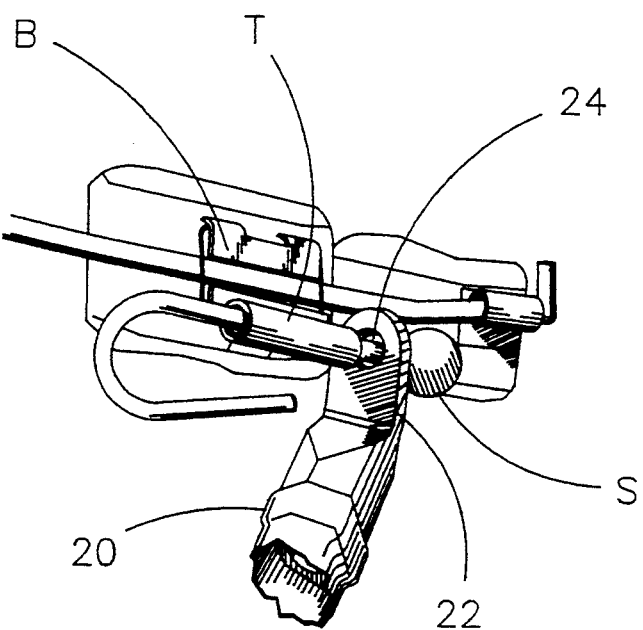
FIG. 6 is an enlarged cutaway perspective view of a non-adjustable end cap of the adjustable bite corrector of this invention as installed on a patient's braces.

FIG. 6 is an enlarged cutaway perspective view of a non-adjustable end cap 20 of the adjustable bite corrector of this invention as installed on a patient's braces B. Eyelet 24 is captured by wire W, molar tube T, and spherical stop S.

Figure 7:
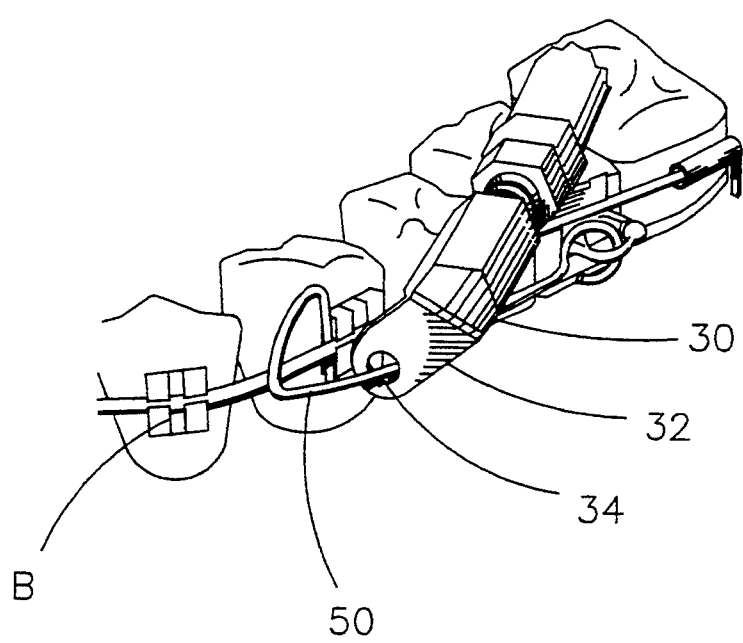
FIG. 7 is an enlarged cutaway perspective view of an adjustable end cap of the adjustable bite corrector of this invention as installed on a patient's braces.

FIG. 7 is an enlarged cutaway perspective view of an adjustable end cap 30 of the adjustable bite corrector of this invention as installed on a patient's braces B. Eyelet 34 is slightably captured by inventive jigwire 50, which permits movement of the eyelet along its length.

Figure 8:
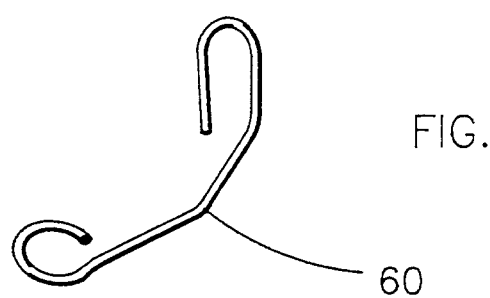
FIG. 8 is a perspective view of an eyelet and hook-type mounting jig.
Figure 9:
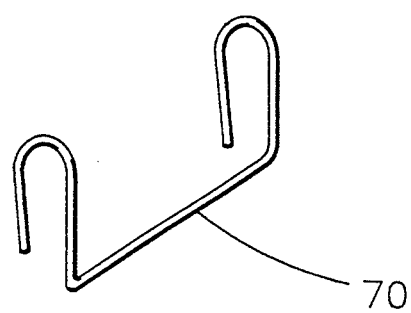
FIG. 9 is a perspective view of a double hook-type mounting jig.
Figure 10:
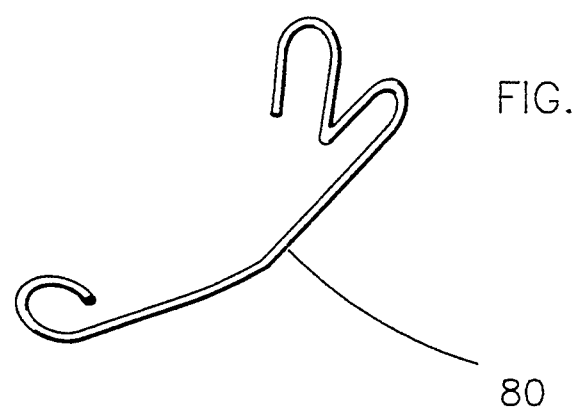
FIG. 10 is a perspective view of an extended horizontal-type mounting jig.
Figure 11:
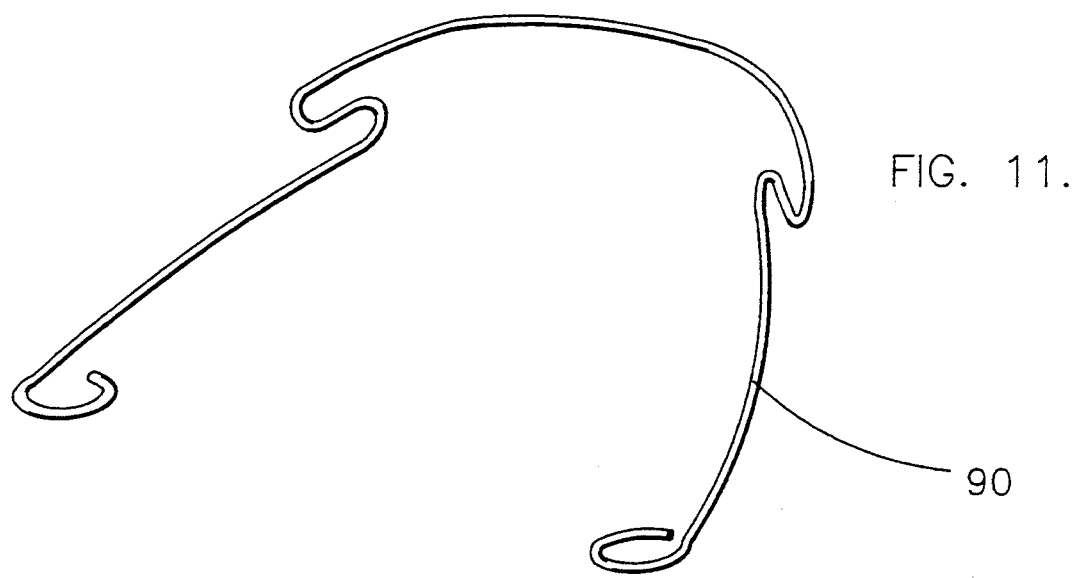
FIG. 11 is a perspective view of an overlay-type mounting jig.

FIG. 8 is a perspective view of an eyelet and hook-type mounting jig 60. FIG. 9 is a perspective view of a double hooktype mounting jig 70. FIG. 10 is a perspective view of an extended horizontal-type mounting jig 80; and FIG. 11 is a perspective view of an overlay-type mounting jig 90.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. An orthodontic appliance for treating an overbite condition in a patient whose upper row of teeth lies abnormally forward of the lower row of teeth in the patient's lower jaw, comprising:
   upper attachment means adapted to be secured to said upper row of teeth;
   lower attachment means adapted to be secured to said lower row of teeth;
   at least one flexible, adjustable-length, stretching appliance element extending between and attached to said upper attachment means and to said lower attachment means and adapted to lie on one side of the patient's jaw, said appliance element having sufficient stiffness to exert a small axial pushing force from end to end when flexed, each said element having end means for bearing against said attachment means while allowing the element to swivel relative to said attachment means;

whereby said appliance element, when installed in a patient's mouth and in a slightly flexed condition, exerts a small pushing force on the patient's upper and lower jaws, tending to correct said overbite condition, said appliance element allowing the patient to move his jaws to talk, chew and cleanse both rows of teeth.

2. An elongated force transmitting but flexible link element for use as an orthodontic appliance for counteracting an abnormal bite condition between a patient's upper and lower rows of teeth by producing a pushing force when flexed, said link element comprising:

a stretchable coiled wire having coils spaced apart along the length thereof;

a pair of end caps attached to opposite ends of said coiled wire, each said end cap having means for connecting said link element with attachment means that are adapted to be on the patient's upper and lower rows of teeth; and an outer layer of stretchable and flexible material covering said coiled wire between said end caps.

3. An orthodontic appliance for treating an underbite condition in a patient whose upper row of teeth lies abnormally rearward of the lower row of teeth in the patient's lower jaw, comprising:

upper attachment means adapted to be secured to said upper row of teeth;

lower attachment means adapted to be secured to said lower row of teeth;

a pair of stretching, adjustable-length, flexible appliance elements extending between and attached to said upper attachment means and said lower attachment means and adapted to lie on one side of the patient's jaw, said elements having sufficient stiffness to exert a small axial pushing force from end to end when flexed, said elements having end means for bearing against said attachment means while allowing the elements to swivel relative to said attachment means;

whereby said appliance elements, when installed and in a slightly flexed condition, exert a small pushing force on the patient's upper and lower jaws, said elements being swivelable at their ends to allow movement thereof so that the patient can move his jaws to talk, chew and cleanse both rows of teeth.

* * * * *